(12) United States Patent
McManus

(10) Patent No.: US 9,024,108 B2
(45) Date of Patent: May 5, 2015

(54) APPARATUS AND METHOD FOR IMPROVED FEMININE SANITARY RETENTION AND ABSORPTION

(76) Inventor: Marcia McManus, Pompano Beach, FL (US)

( * ) Notice: Subject to any disclaimer, the term of this patent is extended or adjusted under 35 U.S.C. 154(b) by 803 days.

(21) Appl. No.: 12/626,944

(22) Filed: Nov. 30, 2009

(65) Prior Publication Data

US 2011/0130733 A1    Jun. 2, 2011

(51) Int. Cl.
| | |
|---|---|
| A61F 13/505 | (2006.01) |
| A61F 13/53 | (2006.01) |
| A61F 13/47 | (2006.01) |
| A61F 13/82 | (2006.01) |
| A61F 13/15 | (2006.01) |
| A61F 13/514 | (2006.01) |

(52) U.S. Cl.
CPC ............ *A61F 13/15268* (2013.01); *A61F 2013/530802* (2013.01); *A61F 2013/530861* (2013.01); *A61F 13/505* (2013.01); *A61F 13/51458* (2013.01); *A61F 13/51478* (2013.01)

(58) Field of Classification Search
CPC ........... A61F 13/53; A61F 2013/53049; A61F 2013/530802; A61F 2013/503839; A61F 2013/530854; A61F 2013/530861
USPC ............ 604/367, 369–373, 378, 385.14, 386, 604/387, 393, 402, 385.101, 385.28
See application file for complete search history.

(56) References Cited

U.S. PATENT DOCUMENTS

| | | | | |
|---|---|---|---|---|
| 4,425,130 | A * | 1/1984 | DesMarais | 604/389 |
| 4,505,707 | A * | 3/1985 | Feeney | 604/393 |
| 4,902,565 | A * | 2/1990 | Brook | 428/315.5 |
| 4,985,467 | A * | 1/1991 | Kelly et al. | 521/52 |
| 5,268,224 | A * | 12/1993 | DesMarais et al. | 442/370 |
| 5,397,316 | A * | 3/1995 | LaVon et al. | 604/369 |
| 5,496,429 | A * | 3/1996 | Hasse et al. | 156/73.3 |
| 5,986,167 | A * | 11/1999 | Arteman et al. | 604/380 |
| 6,160,197 | A * | 12/2000 | Lassen et al. | 604/358 |
| 6,264,776 | B1 * | 7/2001 | DiPalma | 156/73.1 |
| 6,399,854 | B1 * | 6/2002 | Vartiainen | 604/367 |
| 6,592,563 | B2 * | 7/2003 | Mizutani et al. | 604/385.28 |
| 7,842,848 | B2 * | 11/2010 | Janusson et al. | 602/46 |
| 2001/0027304 | A1 * | 10/2001 | Mayer | 604/385.14 |
| 2002/0026167 | A1 * | 2/2002 | Pompa | 604/378 |
| 2002/0143309 | A1 * | 10/2002 | Glasgow et al. | 604/378 |
| 2003/0045848 | A1 * | 3/2003 | Chmielewski | 604/369 |

(Continued)

*Primary Examiner* — Tan-Uyen (Jackie) T Ho
*Assistant Examiner* — Kathryn E Ditmer
(74) *Attorney, Agent, or Firm* — The Miller Law Offices PLC; Steven J. Miller, Esq.

(57) ABSTRACT

An apparatus and method for improved retention and absorption of liquids from female menstrual periods, having multi-elements, wherein the first element has an optionally reusable outer pad retention structure, and the second element has a single use disposable inner pad, said inner pad having unique features, said features rendering said inner pad of being capable of continuously conforming to ever changing exterior vaginal geometries during an individual wearer's active work day, while simultaneously retaining all menstrual liquid within said inner pad and not allowing any leakage into the outer reusable pad, but allowing gas permeability through all elements thereby allowing heat transfer away from the user's body and a more comfortable feminine sanitary device. Further the apparatus and method allow said inner replacement pad to be augmented by an optional breathable inner supplemental replacement pad to retain additional liquid during unusually heavy menstrual liquid flow.

3 Claims, 2 Drawing Sheets

(56) References Cited

U.S. PATENT DOCUMENTS

| | | | |
|---|---|---|---|
| 2006/0184150 A1* | 8/2006 | Noel | 604/383 |
| 2008/0221541 A1* | 9/2008 | Lavash et al. | 604/385.01 |
| 2009/0118691 A1* | 5/2009 | Rosenfeld | 604/385.03 |
| 2010/0057034 A1* | 3/2010 | Dennis et al. | 604/385.05 |

* cited by examiner

APPARATUS AND METHOD FOR IMPROVED FEMININE SANITARY RETENTION AND ABSORPTION

CROSS REFERENCE TO RELATED APPLICATIONS

Not Applicable.

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

1. Field of the Invention

The current invention herein relates to an improved apparatus and method for retaining and absorbing fluids during female menstrual periods comprising a multi-element apparatus and method, wherein the first element consists of an optionally reusable outer pad retention structure, and the second element consists of a single use disposable inner pad, said inner pad, not being an interlabial pad, but rather being a pad that touches the exterior surfaces of the vagina, said inner pad having unique features, said features rendering said inner pad of being capable of conforming to continuously changing vaginal geometries of a particular woman as a woman moves during her daily routine of walking, sitting, exercising, etc., while simultaneously retaining all menstrual liquid within said inner pad and not allowing any leakage into the outer reusable pad, thereby reducing the overall cost to the consumer, since the consumer need only purchase the replacement inner pads, and may reuse the outer structural retention pad. Further the apparatus and method allows for said inner replacement pad to be augmented by a supplemental inner replacement pad, similarly uniquely featured as the regular inner pad, in the event of an extremely heavy menstrual liquid flow. All pads (outer, inner, and supplemental inner) have breathable materials, to allow gas/vapor flow therethrough, thereby allowing for any heat buildup from the user walking, exercising, etc., to be continuously transmitted and vented through natural convection gas/vapor flow from the user's body out to the atmosphere.

2. Prior Art

In the prior art sanitary napkin type articles would consist of single use sanitary napkins or single use tampons. In both devices, the user needed to purchase an entire new sanitary napkin or tampon, each time, the sanitary devices were subjected to menstrual liquid. Some recent single use sanitary pads or napkins did have outer periphery fluid retention features, and there were also developed inter-labial pads which had the ability to conform to the varying interlabial geometry of each female consumer. U.S. Pat. No. 7,307,197 ["197"] discloses an "inter-labial pad" which is actually inserted into and between the wearer's labia and conforms to that interior geometry. Similarly, U.S. Pat. No. 7,329,243 ["243"] discloses an "inter-labial' pad which is, in-fact, "inserted to a point of insertion", between the labia of the wearer. The instant invention is not an 'inter-labial' pad as disclosed in the 197 and 243 patents, but rather a combination apparatus and method comprising an outer and inner pad, said inner pad not being placed or inserted 'inter-labially' but rather affixed over the exterior surfaces of the wearer's vaginal genitalia, and conforming continuously on a real time basis to an individual wearer as the surface geometry of said individual's vaginal genitalia continuously varies, during her active day comprising walking, running, sitting, standing, bending, etc. But none of the prior art had the ability to accommodate the ever changing exterior surface vaginal geometry of a particular female, as said individual goes through her busy full day routine, such as walking, sitting, exercising, etc., while simultaneously capturing all menstrual liquid and simultaneously allowing gas/vapor permeability from the vaginal surfaces of the user then out through all elements of the entire apparatus and ultimately to the atmosphere. The aforesaid unique features are accomplished in a less expensive multi-element inner and outer pad apparatus and method, wherein the inner pad is a less expensive optionally replaceable insert that continuously conforms to the outer surface variations of the vaginal area while simulataneously being capable of completely absorbing and retaining menstrual liquid, and the outer pad has the capability of being a reusable element to house and retain the inner replaceable pad. The inner disposable pad is constructed so as to not allow any menstrual liquid to come in contact with any part of the outer reusable pad. This invention also includes the option for the user to purchase and place an additional supplemental inner pad, to be placed in between the user's exterior vaginal surfaces and the regular inner pad, if the user is experiencing unusually heavy menstrual liquid flows. Further, All pads (outer, inner, and supplemental inner) have breathable materials, to allow gas/vapor flow therethrough, thereby allowing for any heat buildup from the user walking, exercising, etc., to be continuously transmitted and vented through natural convection gas/vapor flow from the user's body out to the atmosphere. This invention improves the consuming women's menstrual liquid retention, in a more effective, more comfortable, more environmentally friendly, and less costly manner. These novel advantages and features are something the women's sanitary napkin and tampon industry has not envisioned and this invention will change the future of the this industry. This apparatus and method is also better for the environment, as the amount of material that is discarded in the replaceable inner pad element, is far less than that of a traditional combined apparatus and method. The consuming female public wants more efficient, more comfortable, more environmentally more friendly, lower cost sanitary products, to handle their monthly menstrual cycles. This invention resolves the aforementioned prior deficiencies.

SUMMARY OF THE INVENTION

The current invention herein comprises an improvement for retaining and absorbing bodily liquids during female menstrual periods, said apparatus and method comprising a multi-element structure, wherein the first element consists of a reusable outer pad retention structure, said outer pad retention structure being made of materials that allow for several days of use and being structurally capable to holding the inner pad in position against the vaginal area of a female user's body, and the second element comprising a single use disposable inner pad, said inner pad having several unique features, said features rendering said inner pad capable of conforming to ever changing exterior vaginal geometries of a user during her daily active routine of walking, exercising, etc., using materials that include a viscoelastic material, while simultaneously being able to absorb and/or adsorb menstrual liquid flows by having granular hydrophilic polymers uniquely combined with said viscoelastic material, so as not to allow any leakage of menstrual liquid into the outer reusable pad by using an inner pad outer layer made of a breathable liquid barrier. Said breathable liquid barrier being capable of stopping and retaining all menstrual liquids, but allowing any gas/vapors to permeate said barrier, to allow for a lower temperature buildup in said structure, and thereby, more comfort for the user. Optionally, at the discretion of the user, the user may purchase and place between her vaginal surfaces and the aforesaid regular inner pad, an additional supplemental inner pad, comprised of the same uniquely combined viscoelastic hydrophilic materials, but not having a liquid barrier back surface (adjacent to the inner surface of the regular inner pad) but yet being gas/vapor permeable for temperature control and comfort, so that any heavy flow excess menstrual liquid within said supplemental inner pad could then traverse onto the regular inner pad for final absorption and/or adsorption. This reduces the overall cost to the consumer, since the consumer need only purchase the replacement inner pads, and may reuse the outer structural retention pad.

DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

In the drawings.

DETAILED DESCRIPTION OF THE EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed structure or manner.

Figure 1:
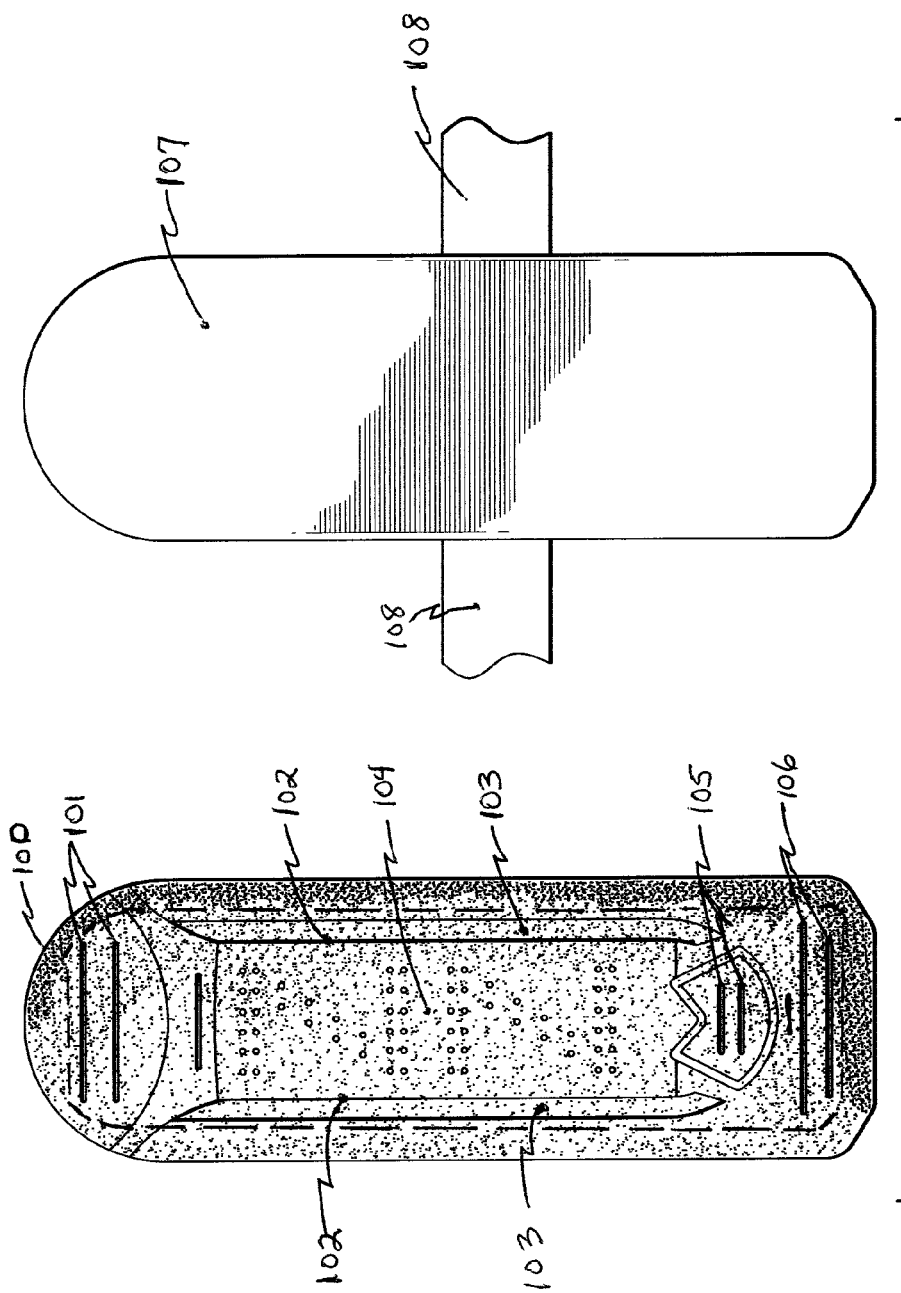
FIG. 1 is a plan view of a preferred embodiment of the invention. The left drawing as viewed depicts the part of the apparatus and method, with both the inner and outer pads assembled, that faces the body of the user, the dashed line depicting the division line between the inner and outer pad elements, whereas the right drawing as viewed depicts the part of said assembled structure that faces away from the body of the user.
Figure 2:
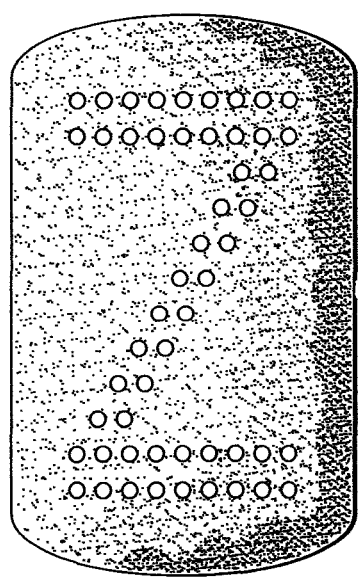
FIG. 2 is a plan view of the optional supplemental replaceable inner pad element of the apparatus.

Reference will now be made in detail to an exemplary embodiment of the apparatus and method, an example which is illustrated in the accompanying drawings (FIG. 1 and FIG. 2).

FIG. 1 is a plan view of the preferred embodiment of the invention. Further, FIG. 1 is divided into two drawings; namely, one on the left as viewed by the reader and one on the right as viewed by the reader. Said left view depicts the fully assembled outer and inner multi-pad structure that would face and touch the body of the female user. The right view depicts the structure that would face out away from, and not touch, the body of the user. The overall shape of the assembled structure consists of a semi-circular arc shaped section at the top of the outer pad (100) element. Note the dashed line on the left view of FIG. 1 has a dashed line, said dashed line represents the actual physical division between the reusable outer pad (100), and the disposable inner pad (104). Just below the top of the outer pad (100) and located within the disposable inner pad (104) are several single cut upper drain canals (101), just below which there is an elongated center section having edge barriers (102) located on the inner pad running vertically at its outer edges to further assist in the collecting and retention of the menstrual liquid, the outer surface of said edge barriers being made of gas/vapor permeable hydrophobic materials to assist in containing the menstrual liquid within the inner pad yet allow gas/vapors to transmit through to ensure heat transfer away from the user's body, in addition, there are vertically running double cut walls with drain passages (103) in said inner replaceable pad also made of gas/vapor permeable hydrophobic materials which are also intended to assist in containing the menstrual liquid within the inner pad yet allow gas/vapors to transmit through to ensure heat transfer away from the user's body, in addition said vertical walls also being used to center and retain the inner replaceable pad (104) within the outer pad (100), said inner replaceable pad having unique hydrophilic polymer impregnated viscoelastic materials within it, and said inner replaceable pad having drain holes cut therein in a "Z" pattern for better menstrual liquid flow and resultant absorption and/or adsorption, and to allow for better gas/vapor permeability to assist in heat transfer away from the user resultant lower temperatures under the inner pad adjacent to the user's exterior vaginal surfaces to increase said user's comfort. Just below said double cut walls with drain passages (103) are lower single cut drain canals (105), and further below which are additional single cut drain canals (106), the outer surface of said canals (105 and 106) being made of gas/vapor permeable hydrophobic materials to assist in containing the menstrual liquid within the inner pad yet allow gas/vapors to transmit through to ensure heat transfer away from the user's body, and to further assist in the collecting and retention of menstrual liquid. The right view of FIG. 1 depicts the liquid resistant outer protective layer (107) made of breathable hydrophobic materials, to allow only for gas/vapor/vapor permeability thereby assisting in maximum temperature control and subsequent user comfort, said liquid resistant outer protective layer (107) facing away from the user's body and touching said user's undergarments. Also depicted in FIG. 1, are the support attachments (108) for securely attaching the entire assembled apparatus to the user's body.

FIG. 2 is a plan view of the supplemental inner reusable pad, which the user may opt to purchase and place between the regular inner pad and the user's vaginal surface area in case said user experiences unusually heavy menstrual liquid flows. This optional supplemental inner pad also has breathable materials, to allow gas/vapor flow therethrough, thereby allowing for any heat buildup from the user to transfer out through natural convection to the atmosphere, and allow for lower temperatures between the inner surface of said supplemental inner pad, and the exterior surfaces of the user's vagina.

This embodiment of the invention provides for improved capture and retention of female menstrual liquids, with greater continuous bodily conformity, better temperature control and subsequent comfort, better environmental sensitivity, and at a reduced price for the consumer.

In an alternate embodiment, the multi-element apparatus and method described above [regular inner pad (104) and outer pad (100)] may be manufactured in one unit, whereby the regular inner pad and outer pads are not separable, thereby requiring replacement of the outer pad when the inner pad is replaced, but still allowing for the optional use of the supplemental inner pad (FIG. 2) in cases of heavy menstrual liquid flows, but the assembled unitary apparatus would still have all of the menstrual liquid retaining, vaginal exterior geometry conforming attributes, and gas/vapor temperature controlling attributes, as the above described preferred embodiment.

In so far as the description above and the accompanying drawings disclose any additional subject matter that is not within the scope of the claims below, the inventions are not dedicated to the public and the right to file one or more applications to claim such additional inventions is reserved.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by more claims to be submitted in a subsequently filed non-provisional application claiming priority from this application.

What is claimed is:

1. An apparatus for absorbing and retaining the menstrual liquid of a female individual, said apparatus comprising:
    a reusable outer pad and a disposable inner pad,
    said reusable outer pad having a liquid resistant outer protective surface that faces away from the user's body and faces the user's garments,
    said outer pad having an inner surface that generally faces towards the user's body, said inner surface defining an inner surface area,
    said reusable outer pad being made of breathable hydrophobic materials,
    said reusable outer pad having support attachments for securely attaching the apparatus to the user's body,
    a disposable single use inner pad, said inner pad having an inner surface that faces and touches the user's body, said inner pad having an outer surface that faces away from the user's body,
    said inner pad being geometrically shaped to fit within the inner surface area of said outer pad,
    said inner pad having a top section and a bottom section, said top section being geometrically located at an end of said inner pad that is configured to be located closer to the user's torso when worn by the user, and said bottom section being geometrically located at an end of said inner pad that is configured to be located closer to the user's legs when worn by the user,
    said disposable inner pad having a plurality of single cut drain canals for assisting in draining and directing liquid away from the user's body,
    said single cut drain canals being a plurality of parallel straight line perforations through the inner surface of said inner pad, said single cut parallel perforations being generally located at the top and bottom sections of said inner pad, said single cut straight line drain canals being generally geometrically oriented along a line that is generally perpendicular to a longitudinal centerline of said inner pad,
    between said top section and bottom section of said inner pad is an elongated center section having double cut drain canals, said double cut drain canals being a plurality of parallel straight line perforations through the inner surface of said inner pad, said double cut drain canals being a plurality of closely spaced parallel straight line perforations through the inner surface of said inner pad, said double cut parallel perforations being generally located between said top and bottom sections of said inner pad, said double cut straight line drain canals being generally geometrically oriented along a line that is generally perpendicular to said single cut drain canals and parallel to the longitudinal centerline of said inner pad,
    said closely spaced double cut drain canals thereby forming edge barriers, said edge barriers located on said inner pad at its outer perimeter boundary, said edge barriers further assisting in the collection and retention of the menstrual liquid,
    said edge barriers being made of breathable hydrophobic materials to assist in containing the menstrual liquid within the inner pad yet allow gas/vapors to transmit through,
    said edge barriers also being used to center and retain the inner pad within said outer pad,
    said inner pad having granular hydrophilic polymers combined with viscoelastic materials thereby allowing said inner pad to continuously conform to the user's changing body surface geometries during said user's movements,
    the outer surface of said inner pad, an outer surface of said inner pad's edge barriers, and an outer surface of said inner pad's single cut drain canals being made of hydrophobic materials to prevent leakage of menstrual liquid into the outer pad,
    said inner pad having drain holes cut therein for better menstrual liquid flow and resultant absorption and/or adsorption, and to allow for better gas/vapor permeability to assist in heat transfer away from the user to result in lower temperatures under the inner pad adjacent to the user's exterior vaginal surfaces to increase said user's comfort.

2. The apparatus as in claim 1, wherein the inner pad's drain holes are located in said elongated center section and are cut in a "Z" pattern.

3. The apparatus as in claim 1, further having a supplemental inner disposable pad, wherein said disposable supplemental inner pad may be used at the user's discretion, said supplemental disposable inner pad being placed between said inner pad and the user's exterior vaginal surfaces and said supplemental disposable inner pad having the same materials as said inner pad.

* * * * *